(12) United States Patent
Sweeney

(10) Patent No.: US 7,736,370 B2
(45) Date of Patent: Jun. 15, 2010

(54) METHOD FOR INTERCONNECTING LONGITUDINAL MEMBERS EXTENDING ALONG A SPINAL COLUMN

(75) Inventor: Thomas Sweeney, Sarasota, FL (US)

(73) Assignee: Zimmer Spine, Inc., Minneapolis, MN (US)

( * ) Notice: Subject to any disclaimer, the term of this patent is extended or adjusted under 35 U.S.C. 154(b) by 1638 days.

(21) Appl. No.: 10/969,124

(22) Filed: Oct. 20, 2004

(65) Prior Publication Data

US 2005/0107789 A1    May 19, 2005

Related U.S. Application Data

(60) Provisional application No. 60/513,013, filed on Oct. 21, 2003.

(51) Int. Cl.
  A61B 17/58    (2006.01)
  A61B 17/60    (2006.01)
  A61F 2/00     (2006.01)

(52) U.S. Cl. .................... 606/104; 606/250; 606/264; 606/279; 600/210

(58) Field of Classification Search ............... 606/61, 606/86, 104, 108, 198, 246, 250–279, 103; 623/17.11; 604/104, 106
See application file for complete search history.

(56) References Cited

U.S. PATENT DOCUMENTS

| | | | |
|---|---|---|---|
| 4,817,110 A | 3/1989 | Tokuda et al. | |
| 5,163,949 A | 11/1992 | Bonutti | |
| 5,197,971 A | 3/1993 | Bonutti | |
| 5,295,994 A | 3/1994 | Bonutti | |
| 5,345,927 A | 9/1994 | Bonutti | |
| 5,454,365 A | 10/1995 | Bonutti | |
| 5,549,607 A * | 8/1996 | Olson et al. | 606/251 |
| 5,601,590 A | 2/1997 | Bonutti et al. | |
| 5,658,272 A * | 8/1997 | Hasson | 606/1 |
| 5,667,520 A | 9/1997 | Bonutti | |
| 5,734,670 A | 3/1998 | Ono et al. | |
| 5,961,499 A | 10/1999 | Bonutti et al. | |
| 6,171,299 B1 | 1/2001 | Bonutti | |
| 6,187,000 B1 | 2/2001 | Davison et al. | |
| 6,338,730 B1 | 1/2002 | Bonutti et al. | |
| 6,358,254 B1 * | 3/2002 | Anderson | 606/103 |
| 6,358,266 B1 | 3/2002 | Bonutti | |
| 6,423,071 B1 * | 7/2002 | Lawson | 606/103 |
| 6,530,926 B1 | 3/2003 | Davison | |
| 6,616,668 B2 * | 9/2003 | Altarac et al. | 606/61 |
| 6,800,084 B2 | 10/2004 | Davison et al. | |
| 7,008,431 B2 * | 3/2006 | Simonson | 606/86 |

(Continued)

FOREIGN PATENT DOCUMENTS

WO    03068083    8/2003

(Continued)

Primary Examiner—Thomas C Barrett
Assistant Examiner—Andrew Yang
(74) Attorney, Agent, or Firm—Crompton, Seager & Tufte, LLC.

(57) ABSTRACT

A method of interconnecting first and second longitudinal members extending along a spinal column of a patient includes inserting an access port into the body of the patient. A transverse connector is moved through the access port. A first end of the transverse connector is connected to the first longitudinal member. A second end of the transverse connector is connected to the second longitudinal member.

14 Claims, 4 Drawing Sheets

U.S. PATENT DOCUMENTS

| | | |
|---|---|---|
| 7,014,608 B2 * | 3/2006 | Larson et al. ............... 600/201 |
| 7,066,937 B2 | 6/2006 | Shluzas |
| 7,144,396 B2 | 12/2006 | Shluzas |
| 2002/0052603 A1 * | 5/2002 | Nichols et al. ................ 606/61 |
| 2002/0068975 A1 | 6/2002 | Teitelbaum et al. |
| 2003/0014068 A1 | 1/2003 | Bonutti et al. |
| 2003/0073998 A1 | 4/2003 | Pagliuca et al. |
| 2005/0273132 A1 | 12/2005 | Shluzas et al. |

FOREIGN PATENT DOCUMENTS

| | | |
|---|---|---|
| WO | 2005065304 | 7/2005 |

* cited by examiner

METHOD FOR INTERCONNECTING LONGITUDINAL MEMBERS EXTENDING ALONG A SPINAL COLUMN

RELATED APPLICATION

This application claims the benefit of U.S. Provisional Application No. 60/513,013, filed Oct. 21, 2003 and is incorporated herein by reference.

FIELD OF THE INVENTION

The present invention relates to a method and a transverse connector for interconnecting first and second longitudinal members extending along a spinal column, and more specifically, to a method and a transverse connector for interconnecting first and second longitudinal members extending along a spinal column during a minimally invasive surgery.

BACKGROUND OF THE INVENTION

Minimally invasive surgery is a procedure in which surgical instruments are inserted through an access port, a tubular structure, a retractor, or a cannula into the body of a patient. A known minimally invasive surgery allows longitudinal members, such as rods, to be connected to vertebrae of a spinal column through an access port. The rods interconnect adjacent vertebrae of the spinal column. While the above described method enables adjacent vertebrae of a spinal column to be fixed relative to each other, the interconnecting of the longitudinal members has heretofore been conducted by a much more invasive open surgical method.

SUMMARY OF THE INVENTION

The present invention relates to a method and a transverse connector for interconnecting first and second longitudinal members extending along a spinal column of a patient. An access port, tubular structure, retractor, or cannula is inserted into the body of the patient. A transverse connector is moved through the access port. A first end of the transverse connector is connected to the first longitudinal member. A second end of the transverse connector is connected to the second longitudinal member.

The transverse connector for interconnecting the first and second longitudinal members includes a first end connectable with the first longitudinal member. A second end is connectable with the second longitudinal member. A connecting rod connected to the first and second ends extends between the first and second ends. The connecting rod is rotatable about a longitudinal axis of the connecting rod relative to the first end and pivotable about a pivot axis extending transverse to the longitudinal axis. A fastener connects the connecting rod to the first end in any one of a plurality of positions about the longitudinal axis of the connecting rod and in any one of a plurality of pivot positions about the pivot axis. The connecting rod is also positionable along the longitudinal axis of the connecting rod relative to the first end. The transverse connector may interconnect longitudinal members extending at an angle of up to approximately 45° relative to each other.

BRIEF DESCRIPTION OF THE DRAWINGS

The foregoing and other features of the present invention will become apparent to one skilled in the art to which the present invention relates upon consideration of the following description of the invention with reference to the accompanying drawings, in which.

DESCRIPTION OF THE INVENTION

The present invention is directed to a method and a transverse connector for interconnecting first and second longitudinal members extending along a spinal column of a patient. The method involves the use of an access port, a tubular structure, a retractor, or a cannula during a minimally invasive surgery.

Figure 1:
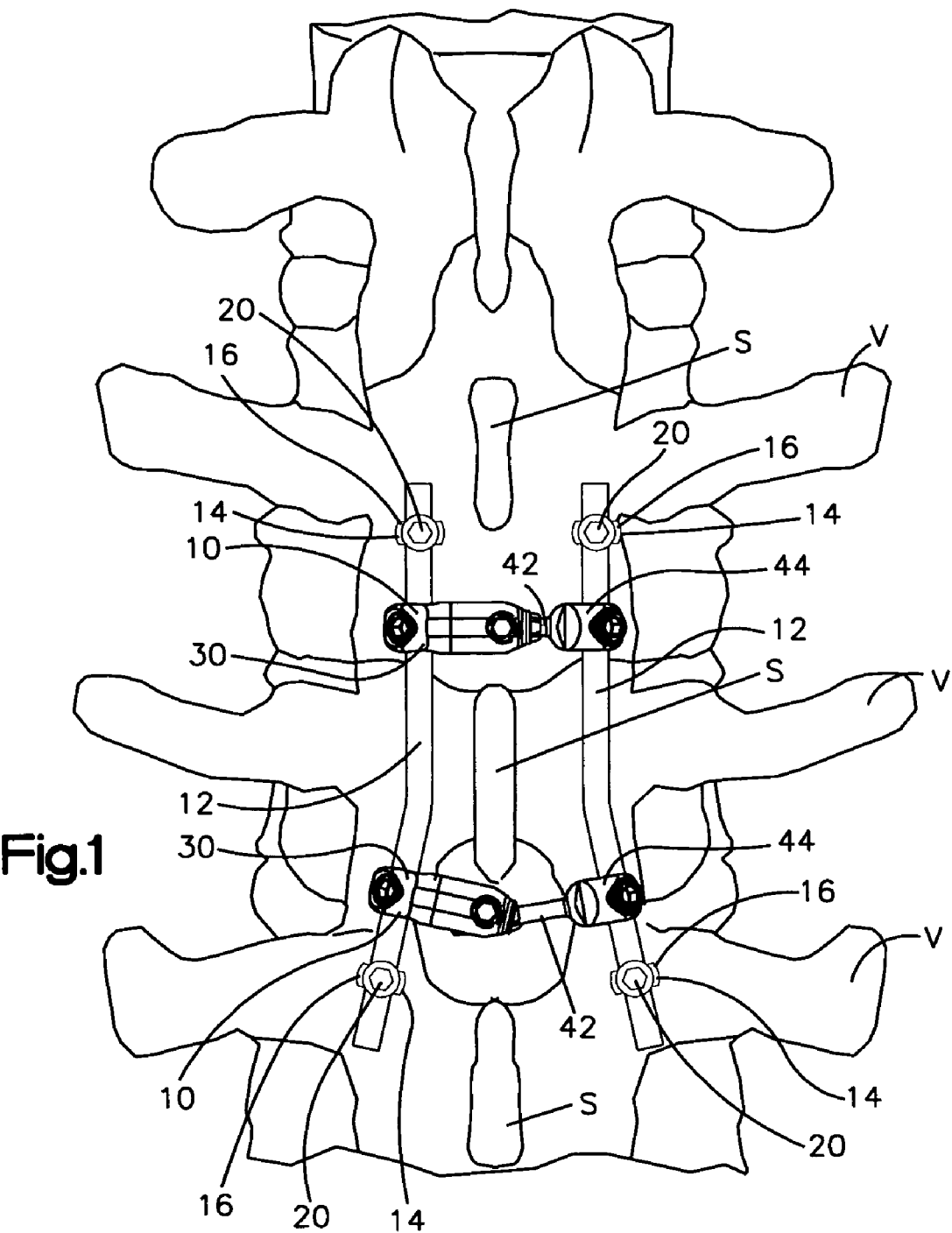
FIG. 1 is an enlarged plan view of transverse connectors of the present invention interconnecting a pair of longitudinal members which are connected to a spinal column.
Figure 2:
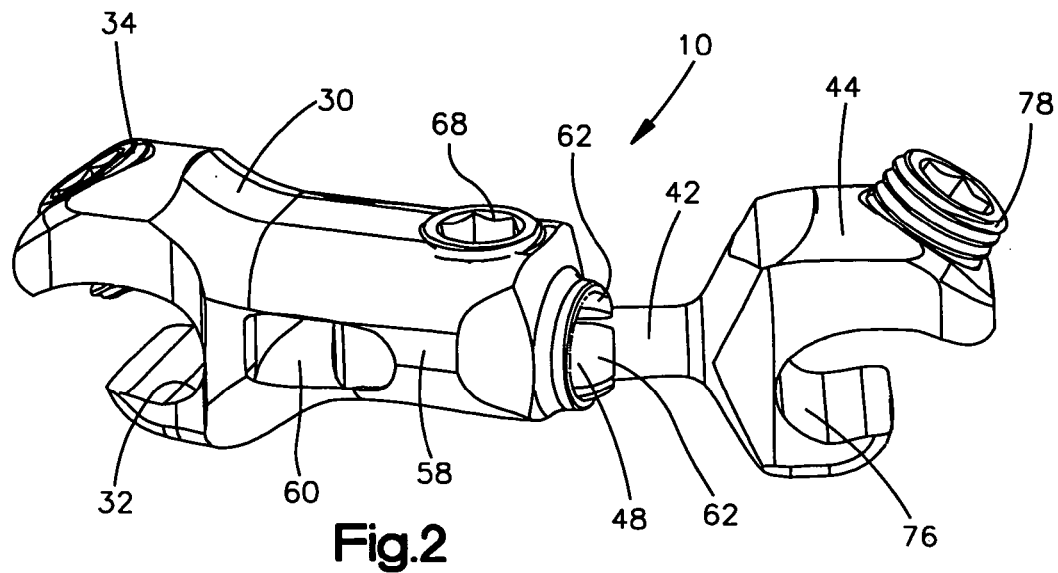
FIG. 2 is a pictorial view of the transverse connector in FIG. 1.
Figure 3:
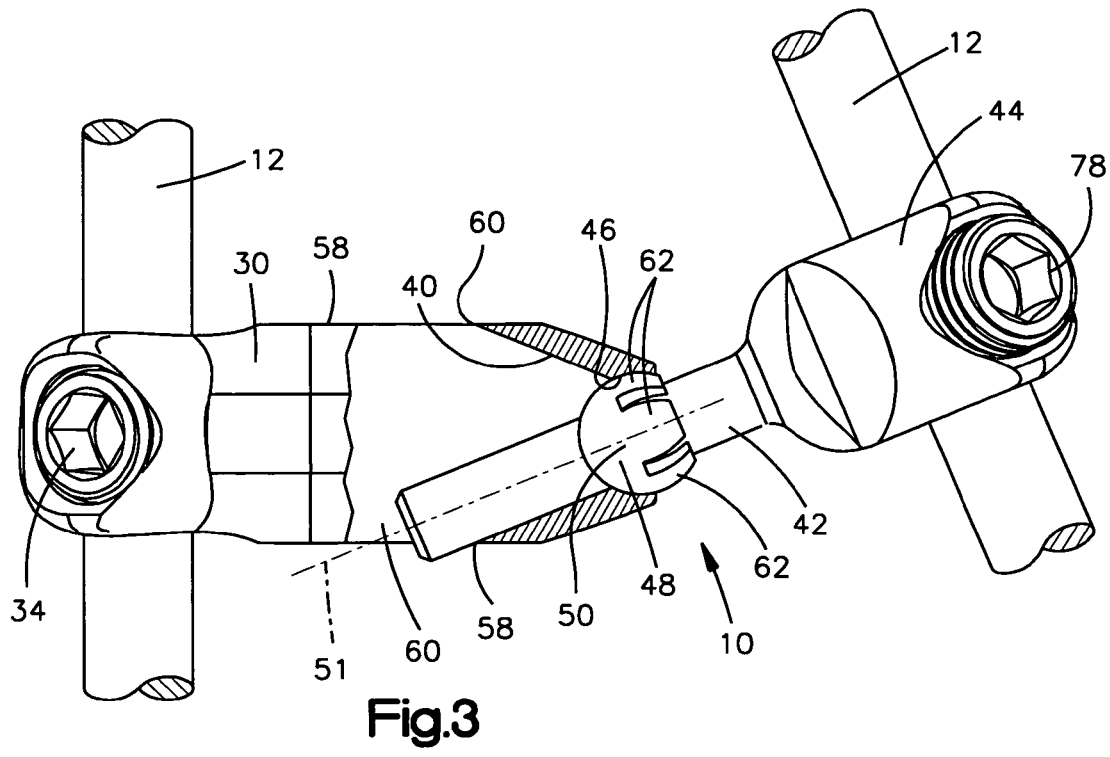
FIG. 3 is an enlarged plan view of the transverse connector of FIG. 1 with portions cut away to show how a connecting rod of the transverse connector is pivoted relative to a first end of the transverse connector.

A transverse connector 10 for interconnecting a pair of longitudinal members or rods 12 connected to vertebrae V of a spinal column is illustrated in FIGS. 1-3. Although the transverse connector 10 is shown interconnecting rods 12, it is contemplated that the transverse connector may interconnect any suitable longitudinal member, such as plates or hexagonal-shaped rods. The rods 12 may be located anywhere along the spinal column and the location of the rods illustrated in FIG. 1 is for example purposes.

Each of the rods 12 (FIG. 1) is elongate and has a sufficient length to span at least two vertebrae V. A plurality of connectors 14 connect the rods 12 with the vertebrae V. The connectors 14 may be of any known or desired configuration. One suitable connector 14 is similar to a connector shown in U.S. patent application Ser. No. 10/075,668, filed Feb. 13, 2003, incorporated herein entirely by reference. Other suitable connectors are shown in PCT Application No. US03/04361, filed Feb. 13, 2003, and U.S. patent application Ser. No. 10/483,605, filed Jan. 13, 2004, which are incorporated herein entirely by reference.

Figure 4:
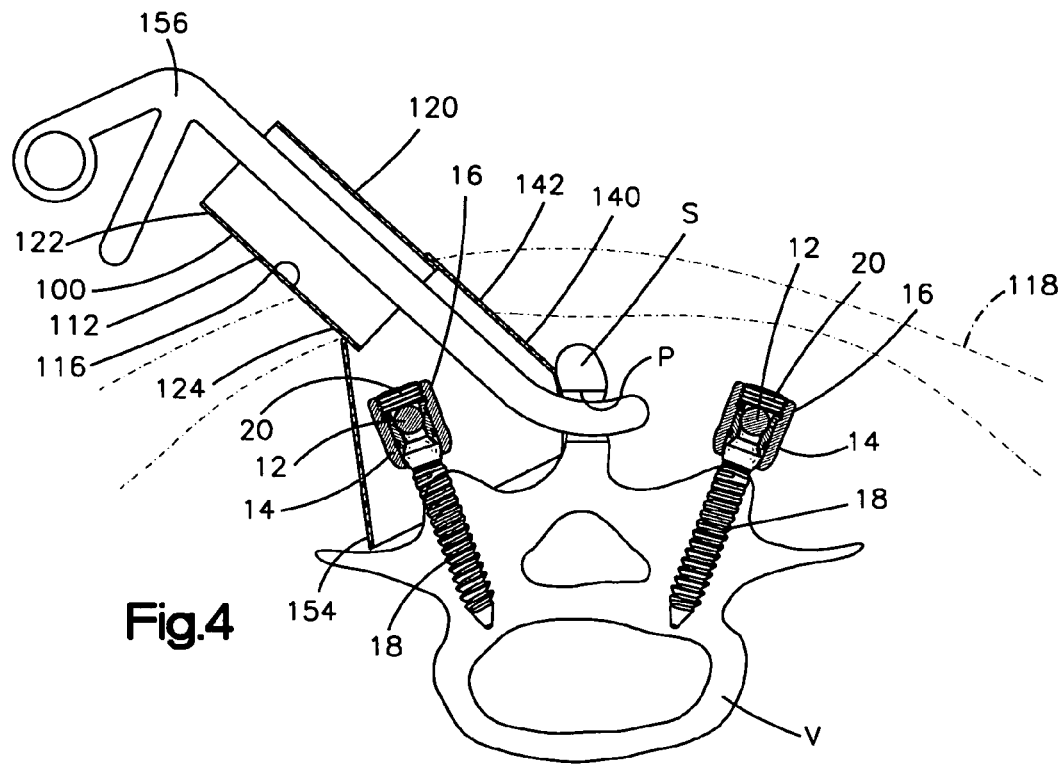
FIG. 4 is a schematic sectional view showing an access port during a minimally invasive surgical procedure for interconnecting the longitudinal members with the transverse connector of FIG. 2.

The connectors 14 (FIG. 4) include housings 16 pivotable relative to fasteners 18. Set screws 20 threadably engage the housings 16 to clamp the rods 12 to the housings and prevent relative movement between the housings and the fasteners 18.

At least one transverse connector 10 (FIG. 1) interconnects the rods 12. The transverse connector 10 blocks relative movement of the rods 12 so that the vertebrae V connected to the rods are maintained in their desired relative positions and do not pivot relative to an anterior/posterior axis or a longitudinal central axis of the spinal column. The transverse connector 10 increases the torsional strength of the rod construct to provide stability when the spinal column twists, such as when the shoulders are turned or angled relative to the legs in a standing position. The transverse connector 10 may be located anywhere along the rods 12 and any number of transverse connectors may be used.

The transverse connector 10 (FIGS. 1-3) includes a first connecting end 30 connectable with one of the spine rods 12. The first end 30 (FIG. 2) has a recess 32 that receives a portion of the spine rod 12. A clamping member or set screw 34 threadably engages the first end 30 and clamps the spine rod 12 to the first connecting end 30 in the recess 32.

The first connecting end 30 (FIG. 3) has an opening 40 that extends through a portion of the first connecting end. The opening 40 receives a connecting rod 42 fixedly connected to a second connecting end 44 and extending from the second connecting end 44. The connecting rod 42 is integrally formed with the second end 44. The opening 40 defines a socket 46 for receiving a ball 48 to define a ball joint 50. The connecting rod 42 extends through the ball 48 and into the opening 40 in the first end 30. The connecting rod 42 is rotatable about a longitudinal axis 51 of the connecting rod and pivotable about a pivot axis extending transverse to the longitudinal axis. The connecting rod 42 may pivot about the pivot axis so that the transverse connector 10 may interconnect rods 12 extending up to approximately 45° relative to each other. The connecting rod 42 is also slidable relative to the ball 48 along the axis 51 and thus is positionable in any one of a plurality of positions along the longitudinal axis 51 relative to the first connecting end 30 and the ball 48.

The first connecting end 30 includes sidewalls 58 that extend generally parallel to each other and transverse to the rod 12 when the rod 12 is connected to the connecting end 30. Each of the walls 58 includes an opening 60. The openings 60 extend through the walls 58 and intersect the opening 40. The connecting rod 42 may extend through the openings 60 in the sidewalls 58, as shown in FIGS. 2 and 3.

The ball 48 has four tabs 62 engageable with the connecting rod 42. A set screw 68 threadably engages the first connecting end 30 and clamps the connecting rod 42 against the connecting end 30 to prevent movement of the connecting rod relative to the connecting end. Accordingly, the set screw 68 connects the connecting rod 42 to the first connecting end 30 in any one of a plurality of positions about the longitudinal axis 51, in any one of a plurality of pivot positions about the pivot axis, and in any one of a plurality of positions along the longitudinal axis 51 of the connecting rod. It is contemplated that the connecting rod 42 could threadably engage the ball 48 to position the connecting rod relative to the ball.

The second connecting end 44 (FIG. 2) has a recess 76. The recess 76 receives a portion of the other spine rod 12. A clamping member or set screw 78 threadably engages the second connecting end 44 and clamps the spine rod 12 to the second connecting end 44 in the recess 76.

When the transverse connector 10 is to be connected to the spine rods 12, the connecting rod 42 is placed through the ball 48. The connecting rod 42 is positioned relative to the connecting end 30. Once the connecting ends 30 and 44 have been positioned relative to each other and the spine rods 12, the rods 12 are placed in the recesses 32 and 76. The set screws 34, 68, and 78 are tightened to connect the connecting rod 42 to the connecting end 30 and the transverse connector 10 to the spine rods 12.

The transverse connector 10 may be moved through a device for providing access to a surgical location, such as an access port, tubular structure, retractor, or cannula 100 to connect the transverse connector to the rods 12. The access port, tubular structure, retractor, or cannula may have any desired configuration. One suitable cannula 100 is similar to a cannula shown in U.S. Pat. No. 6,187,000, incorporated herein entirely by reference. U.S. patent application Ser. No. 09/772,605, filed Jan. 30, 2001, incorporated herein entirely by reference, discloses other cannula structures that may be used. U.S. patent application Ser. No. 10/926,840, filed Aug. 26, 2004, is also incorporated herein entirely by reference.

The cannula 100 is a tubular structure 112 defining a passage 116 through the cannula. Surgical instruments and an endoscope may be inserted into a patient's body 118 through the passage 116 during a minimally invasive surgery to interconnect the longitudinal members 12 with the transverse connector 10.

The tubular structure 112 includes a first or proximal tubular portion 120 and a second or distal tubular portion 140 attached to the first tubular portion. The first tubular portion has a proximal end 122 and a distal end 124. The second tubular portion 140 is pivotally connected to the distal end 124 of the first tubular portion 120. The second tubular portion 140 includes a segment 142 of sheet stock. The segment 142 is rolled in an overlapping manner to form the tubular configuration of the second tubular portion 140. The second tubular portion 140 of the tubular structure 112 is expandable from a contracted condition to an expanded condition shown in FIG. 4. In the contracted condition, the second tubular portion 140 is cylindrical in shape. In the expanded condition, the second tubular portion 140 has a frustoconical configuration.

During a minimally invasive surgical procedure, the cannula 100 (FIG. 4) may be inserted over a tissue dilator or obturator into the body of a patient in the contracted condition. The dilator is removed and an expansion tool (not shown) is inserted into the passage 116 into the cannula 100 to expand the second tubular portion 140. The expansion tool is then removed from the cannula 100 so that one or more surgical instruments and the transverse connector 10 can be inserted through the cannula and inserted into the patient's body 118. The expanded tubular portion 140 can dilate and locally retract and separate spinalis muscle and soft tissues from the vertebrae V thereby creating an operating field at the surgical site.

The rods 12 may be connected to the vertebrae V by the connectors 14 during a minimally invasive surgery. One suitable minimally invasive method for connecting the rods 12 to the vertebrae V is described in U.S. Pat. No. 6,530,926, incorporated herein entirely by reference. A first cannula 100 is inserted into the body of the patient 118. A first fastener 18 is moved through the cannula 100 and secured to a first vertebra V. A second fastener 18 is moved through the cannula 100 and secured to a second vertebra V. A first longitudinal member or rod 12 is moved through the cannula 100. The first rod 12 is connected to the first and second fasteners 18 by clamping members 20. A second cannula 100 is inserted into the body of the patient 118. A third fastener 18 is moved through the cannula 100 and secured to the first vertebra V. A fourth fastener 18 is moved through the second cannula 100 and secured to the second vertebra V. A second longitudinal member or rod 12 is moved through the second cannula 100. The second rod 12 is connected to the third and fourth fasteners 18 by clamping members 20. It is contemplated that any number of fasteners may be moved through the first and second cannula 100 to fix any number of vertebrae of a patient together.

Figure 5:
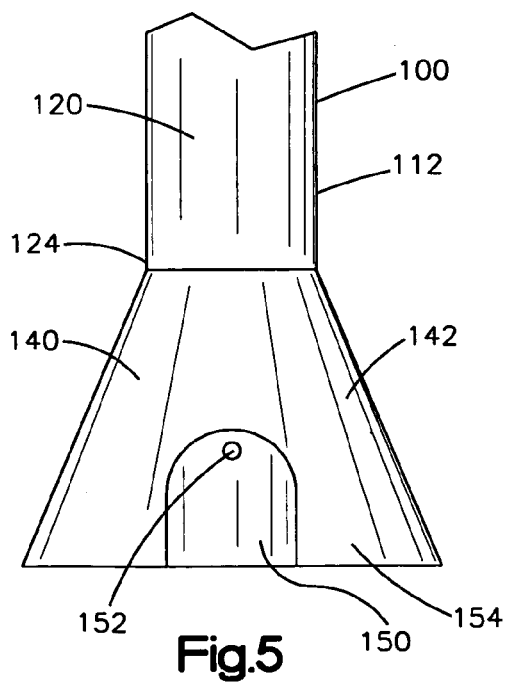
FIG. 5 is a schematic view of an access port for use during the surgical procedure to interconnect the longitudinal members with the transverse connector.

After the rods 12 are connected to the vertebrae V, at least one transverse connector 10 is moved through the second cannula 100 and connected to the rods. The second tubular portion 140 (FIGS. 4 and 5) of the cannula 100 may include a door member 150 pivotally connected to the segment 142 by a fastener 152. The door 150 may be pivoted relative to the segment 142 to uncover a second passage or opening at a distal end 154 of the second tubular portion 140 through which a surgical instrument 156 (FIG. 4), such as a side cutting Kerrison bone removal instrument, may extend. The opening at the distal end 154 extends transverse to the passage 116. The surgical instrument 156 may extend through the opening in the second tubular portion 140 to remove tissue, such as portions of a spinous process S, intraspinous ligament, and/or lamina, to create a passage P from one side of the spine mid-line to the other. After the portions of the spinous process S, intraspinous ligament, and/or lamina have been removed, the transverse connector 10 may be moved through the cannula 100 and into the passage P. The transverse connector 10 extends through the passage P from one side of the spine mid-line to the other. The ends 30 and 44 of the transverse connector 10 are connected to the rods 12 to interconnect the rods 12.

Figure 6:
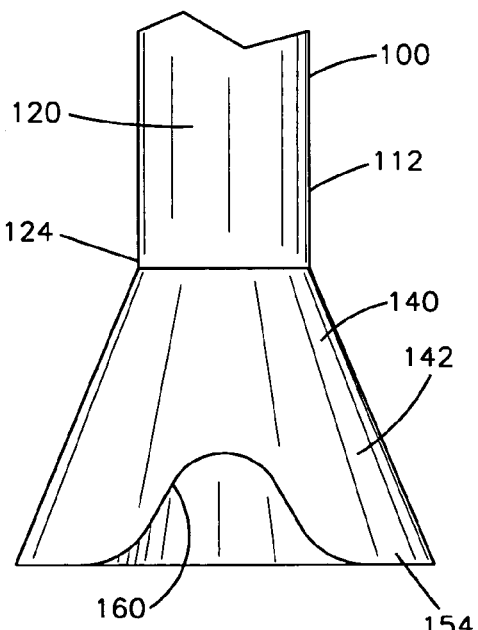
FIG. 6 is a schematic view of another access port for use during the surgical procedure to interconnect the longitudinal members with the transverse connector.

The cannula 100 may have a second passage or recess 160 (FIG. 6) formed in the distal end 154 of the second tubular portion 140. The recess 160 extends transverse to the passage 116. The surgical instrument 156 may extend through the recess 160 in the second tubular portion 140 to remove tissue, such as portions of a spinous process S, intraspinous ligament, and/or lamina, to create a passage P from one side of the spine mid-line to the other. After the portions of the spinous process S, intraspinous ligament, and/or lamina have been removed, the transverse connector 10 may be moved through the cannula 100 and into the passage P. The transverse connector 10 extends through the passage P from one side of the spine mid-line to the other. The ends 30 and 44 of the transverse connector 10 are connected to the rods 12 to interconnect the rods 12.

Figure 7:
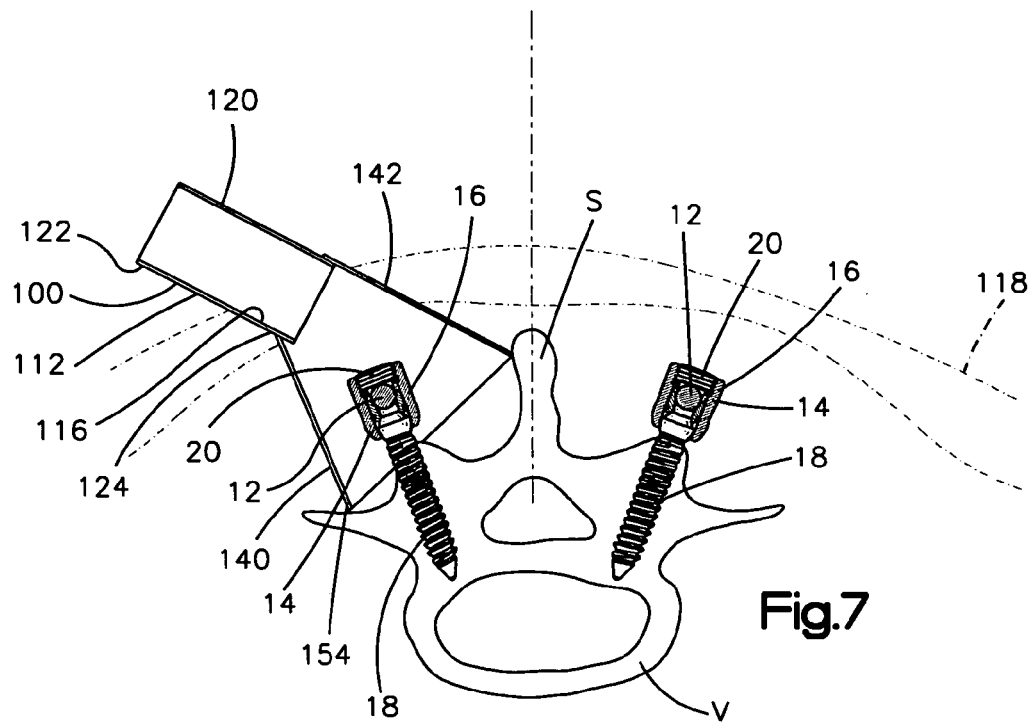
FIG. 7 is a schematic sectional view showing another access port during a surgical procedure for interconnecting the longitudinal members with the transverse connector.

The cannula 100 may be angled obliquely, as shown in FIG. 7, to provide access to the spinous process S, intraspinous ligament, and/or lamina. The surgical instrument 156 may be inserted through the second tubular portion 140 to remove tissue, such as portions of the spinous process S, intraspinous ligament, and/or lamina, to create a passage from one side of the spine mid-line to the other. After the passage is formed, the transverse connector 10 may be moved through the cannula 100 and into the passage. The transverse connector 10 extends through the passage and is connected to the rods 12 to interconnect the rods 12.

Figure 8:
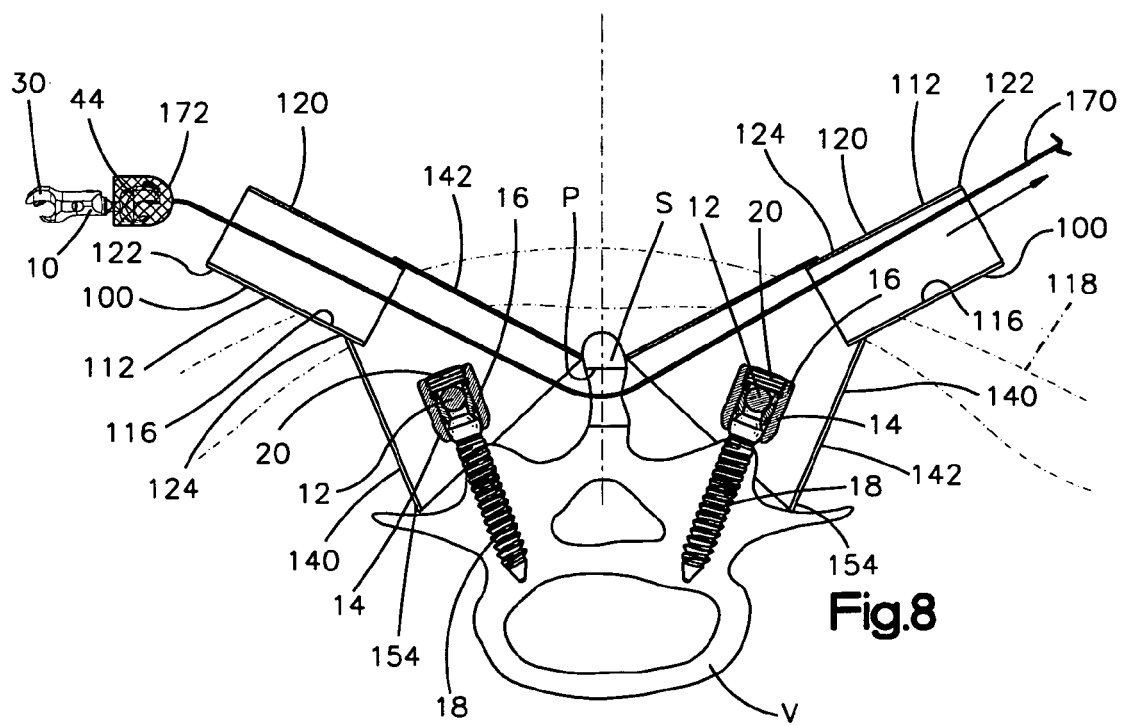
FIG. 8 is a schematic sectional view showing first and second access ports during a surgical procedure for interconnecting the longitudinal members with the transverse connector.

After the first and second rods 12 are connected to the vertebrae through the first and second cannula 100, the first and second cannula 100 may be angled obliquely, as shown in FIG. 8, to provide access to the spinous process S, intraspinous ligament, and/or lamina. The surgical instrument 156 may be inserted through the second tubular portion 140 of one of the first and second cannula 100 to remove tissue, such as portions of the spinous process S, intraspinous ligament, and/or lamina, to create a passage P. After the passage P is formed, the transverse connector 10 may be moved through one of the first and second cannula 100 and into the passage P. The transverse connector 10 extends through the passage P and is connected to the rods 12 to interconnect the rods 12.

A tether 170 may be connected to the transverse connector 10 by a suitable connecting device 172. The transverse connector 10 may be inserted axially into the connecting device 172. The connecting device 172 may grip the transverse connector 10 when the connecting device is pulled to try and remove the connecting device from the transverse connector, similar to a Chinese finger trap device.

The tether 170 may extend through the first and second cannula 100 and the passage P formed in the spinous process S, intraspinous ligament, and/or lamina. The tether may be pulled to guide the transverse connector 10 through the first cannula 100 and into the passage P. Once the transverse connector 10 is inserted through the passage P, the connecting device 172 may be removed from the transverse connector 10. The connecting ends 30 and 44 may be connected to the rods 12 to interconnect the rods.

Although the cannula 100 is shown as having an expandable tubular portion 140, it is contemplated that any suitable access port, tubular structure, retractor, or cannula, such as a tubular conduit having a large enough passage for receiving the transverse connector 10, may be used during the minimally invasive surgery. It is also contemplated that any other suitable device for interconnecting the rods 12 may be used to interconnect the longitudinal members during the minimally invasive surgery.

It will be understood that the above description of the present invention is susceptible to various modifications, changes, and adaptations, and the same are intended to be comprehended within the meaning and range of equivalents, of the appended claims. The presently disclosed embodiments, are considered in all respects to be illustrative and not restrictive. The scope of the invention indicated by the appended claims, rather than the foregoing description, and all changes that come within the meaning and range of equivalence thereof are intended to be embraced therein.

Having described the invention, I claim:

1. A method of interconnecting first and second longitudinal members extending along a spinal column of a patient, said method comprising:
    inserting an access port into a body of the patient, the access port having a recess in a distal portion;
    moving a first fastener through the access port and securing the first fastener to a first vertebra of the spinal column;
    moving a second fastener through the access port and securing the second fastener to a second vertebra of the spinal column;
    moving the first longitudinal member through the access port and connecting the first longitudinal member to the first and second fasteners;
    inserting a second access port into the body of the patient;
    moving a third fastener through the second access port and securing the third fastener to the first vertebra of the spinal column;
    extending an instrument through the recess and removing tissue to create a passage from one side of a mid-line of the spinal column to another side of the mid-line of the spinal column;
    moving a transverse connector through the access port;
    connecting a first end of the transverse connector to the first longitudinal member; and
    connecting a second end of the transverse connector to the second longitudinal member.

2. A method as defined in claim 1 including expanding a portion of said access port.

3. A method as defined in claim 1 including expanding the distal portion of the access port.

4. A method as defined in claim 1 including covering the recess in the distal portion of the access port with a door.

5. A method as defined in claim 4 including pivoting the door relative to the access port to uncover the recess.

6. A method as defined in claim 1 including extending the transverse connector through the passage.

7. A method as defined in claim 1 including angling the access port obliquely.

8. A method as defined in claim 1 including connecting a tether to the transverse connector.

9. A method as defined in claim 8 including extending the tether through the access port and the passage from one side of a mid-line of the spinal column to another side of the mid-line of the spinal column.

10. A method as defined in claim 9 including pulling the tether through the passage to pull the transverse connector into the passage.

11. A method as defined in claim 10 including removing the tether from the transverse connector after the transverse connector is pulled into the passage.

12. A method as defined in claim 11 including inserting a second access port into the body of the patient and extending the tether through the second access port.

13. A method as defined in claim 1 including moving a fourth fastener through the second access port and securing the fourth fastener to the second vertebra of the spinal column.

14. A method as defined in claim 13 including moving the second longitudinal member through the second access port and connecting the second longitudinal member to the third and fourth fasteners.

* * * * *